United States Patent [19]

Persson

[11] 4,117,341
[45] Sep. 26, 1978

[54] CONTROL MEANS

[75] Inventor: Staffan B. Persson, Kenmore, N.Y.

[73] Assignee: American Optical Corporation, Southbridge, Mass.

[21] Appl. No.: 710,774

[22] Filed: Aug. 2, 1976

[51] Int. Cl.² .................. G01N 21/30; A61B 3/00; A61B 3/10
[52] U.S. Cl. .................................. 250/561; 351/1; 351/6
[58] Field of Search ............. 250/561, 231 R, 221, 250/222; 351/1, 6

[56] References Cited

U.S. PATENT DOCUMENTS 1,976,611  10/1934  Gulliksen ..................... 250/561
3,673,414  6/1972  Taniguchi ..................... 250/561

Primary Examiner—Paul A. Sacher
Assistant Examiner—Rodney B. Bovernick
Attorney, Agent, or Firm—Jeremiah J. Duggan; Alan H. Spencer

[57] ABSTRACT

An occluder for interrupting an energy beam is used to control the direction of travel and to stop a moveable member at a reference position from any position remote thereto.

4 Claims, 5 Drawing Figures

CONTROL MEANS

BACKGROUND OF THE INVENTION

This invention relates to an apparatus for returning a movable member from a remote position to a reference position. More particularly, this invention relates to an occluder which controls the direction of travel of a moveable member and determines the location of a reference position of the moveable member.

In various types of instrumentation, particularly ophthalmic instruments, such as an optometer it is frequently desirable to be able to automatically return a moveable member, such as a carriage, to a known reference position.

It is an object of the present invention to provide an apparatus for automatically returning a carriage to a reference position.

It is a further object of the present invention to provide an occluder for determining the direction required to move the carriage to a reference position.

It is still another object of the present invention to use an occluder in combination with an energy beam for determining the location of the reference position of the carriage.

PREFERRED EMBODIMENT

Figure 1:
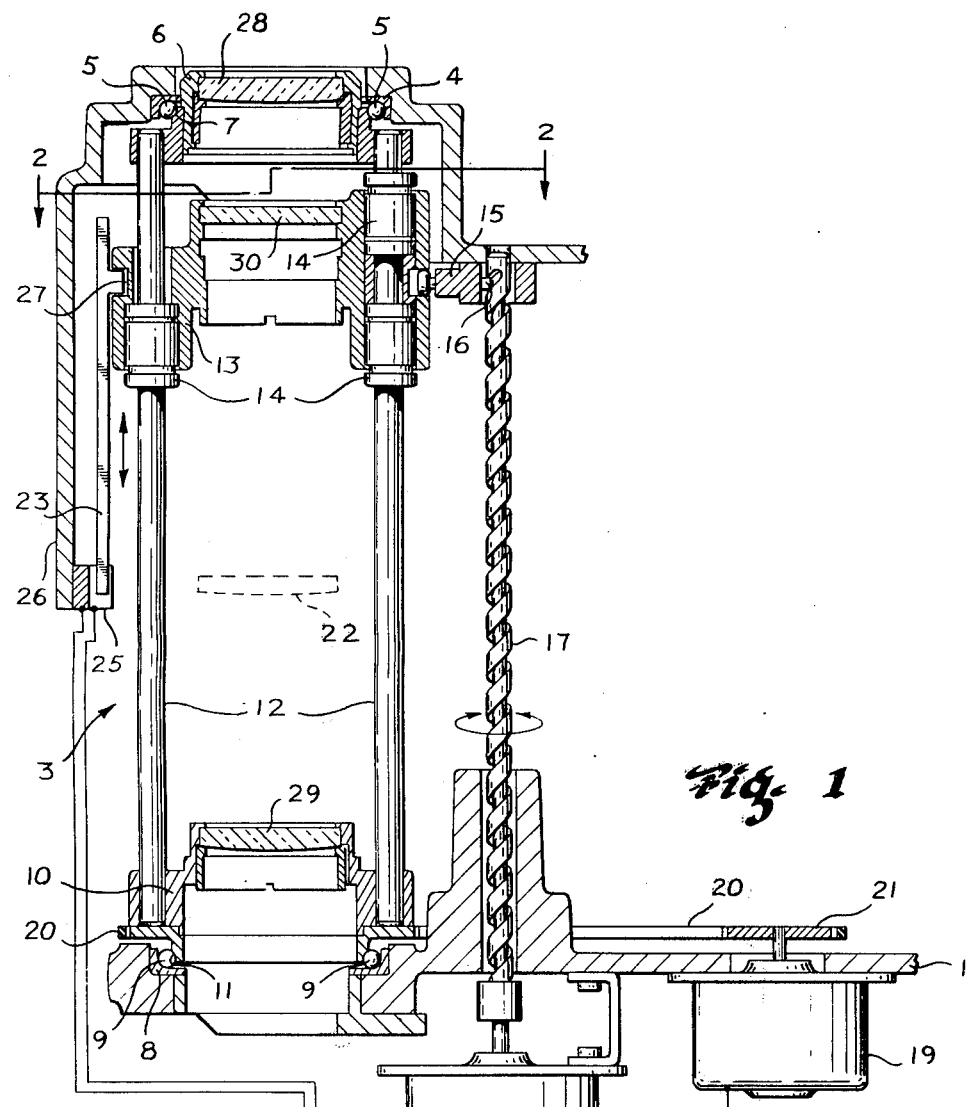
FIG. 1 is a side view, partly in section, of the preferred embodiment of the present invention.
Figure 2:
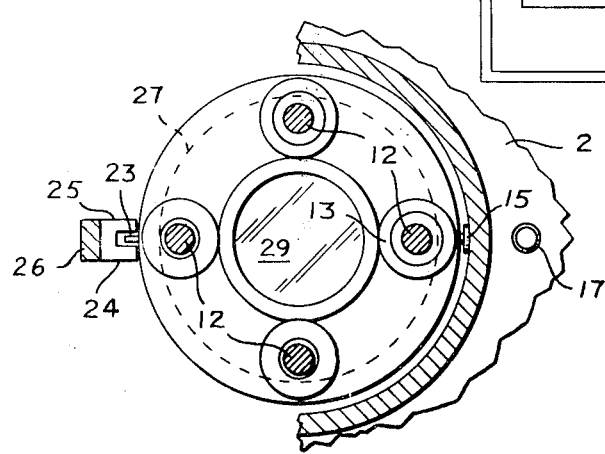
FIG. 2 is a top view in section along line 2—2 of FIG. 1.

Referring to FIG. 1, a device having a frame with lower frame portion 1 and upper frame portion 2 has an optical assembly designated generally by 3. The upper frame portion 2 has outer race 4 positioned therein. Ball bearings 5 rotatably support upper lens mount 6 by inner race 7. Lower frame portion 1 supports outer race 8. Ball bearings 9, in conjunction with outer race 8, rotatably position lower lens mount 10 by inner race 11. Shafts 12 connect upper lens mount 6 and lower lens mount 10 to maintain a fixed spacing therebetween and join the lens mounts for concurrent rotation thereof. Carriage 13 is slideably mounted by bearings 14 on shafts 12. Follower 15 has pin 16 operatively engaging threaded shaft 17. Threaded shaft 17 is rotated in either direction by cylinder motor 18 to selectively move carriage 13 along shafts 12. Axis motor 19 rotates optical assembly 3 via belt 20 and pulley 21 to selectively position the principal meridians.

The apparatus described above carries a pair of cylinder lenses 28 and 29 having a combined focal power in a principal meridian. Cylinder lens 30 has a cylinder power equal to the combined cylinder power of lenses 28 and 29 in a principal meridian normal to the principal meridian of lenses 28 and 29. The focal power in the principal meridian of cylinder lens 30 is varied by movement of carriage 13 along shafts 12. A reference position 22 designates the location of cylinder lens 30 when the focal power in both principal meridians is the same. As cylinder lens 30 moves away from reference position 22, the power along its principal meridian is continuously increased.

Figure 3:
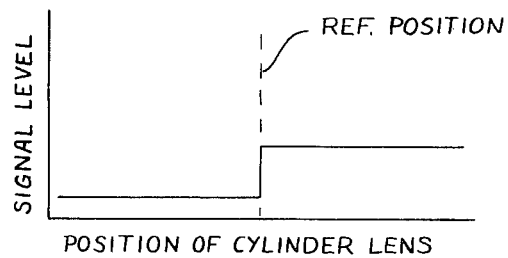
FIG. 3 is a graphic representation of signal level generated by a detector in the device.

It is frequently desirable to be able to return a member moveable in either direction along a path to a reference position. Referring again to FIG. 1, reference position 22 represents a chosen position to which it is frequently desired to return lens 30. Occluder 23 is connected to follower 15 which engages groove 27 in carriage 13 to permit rotation of optical assembly 3. Occluder 23 extends parallel to the path traveled by carriage 13 along shafts 12. An energy beam such as that from IR emitter 25 is positioned on support 26 adjacent to the path traveled by occluder 23. Detector 24 is positioned by support 26 on the opposite side of the path traveled by occluder 23. The energy beam emitted by IR emitter 25 is blocked by occluder 23, if cylinder lens 30 is above reference position 22. If cylinder lens 30 is below reference position 22, detector 24 produces a signal generated by the unoccluded light beam. FIG. 3 is a graphic repesentation of the signal produced by detector 24 plotted against the position of cylinder lens 30. When cylinder lens 30 is positioned above reference position 22 and the control is activated to return cylinder lens 30 to the reference position, the control means will direct motor 18 to rotate counterclockwise because the light beam is blocked by occluder 23 until detector 24 receives light from emitter 25. A signal indicating light is being received by detector 24 which causes the control to stop motor 18. When cylinder lens 30 is below reference position 22 and the control is activated to return cylinder lens 30 to the reference position, the presence of a singal from detector 24 is acted upon by the control to direct motor 18 to run clockwise driving cylinder lens 30 toward reference position 22. As soon as the light beam from IR emitter 25 is interrupted by occluder 23, the control stops motor 18. Thus, activation of the control will directly return cylinder lens 30 to the reference position from any position of carriage 13 along shafts 12.

Alternate Embodiment

Figure 5:
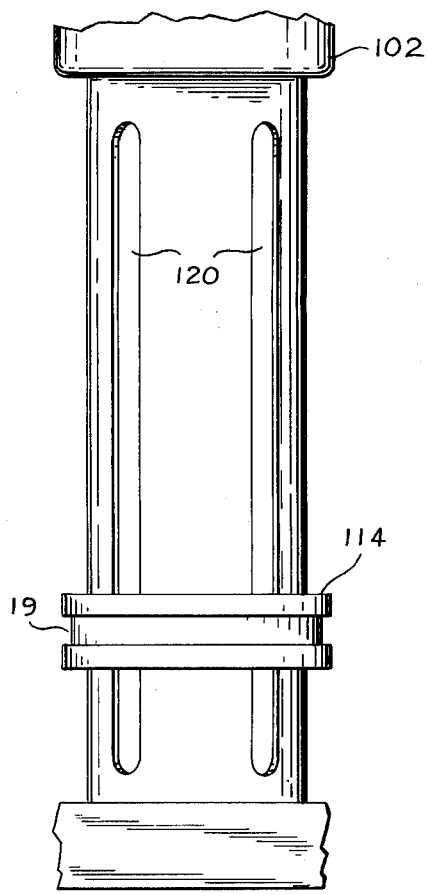
FIG. 5 is a side view showing the exterior of the alternate emodiment.
Figure 4:
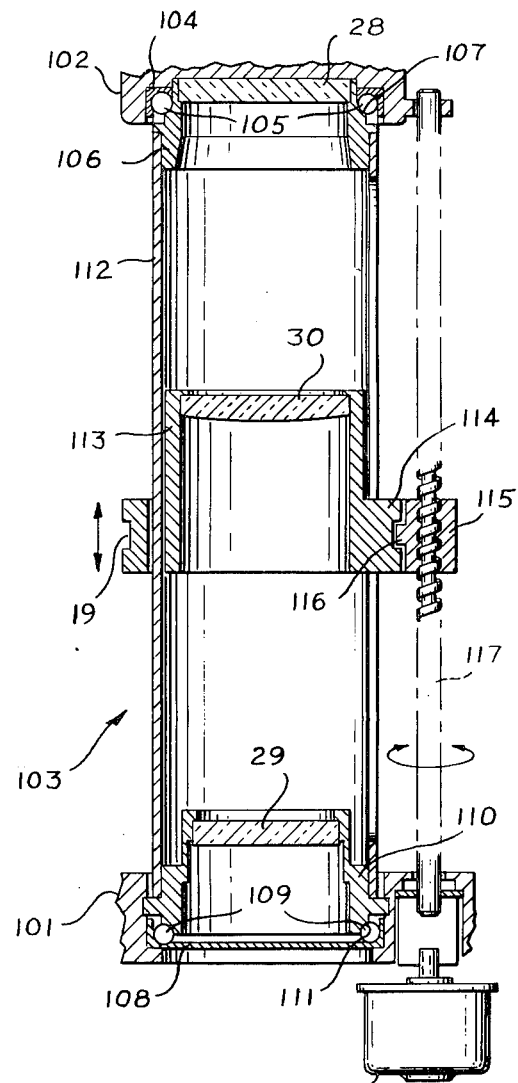
FIG. 4 is a side view of a second embodiment, shown partly in section.

Referring to FIGS. 4 and 5, lower frame portion 101 has an outer race 108 which supports optical assembly 103 by ball bearings 109 which carry lower lens mount 110 by a machine surface 111 acting as an inner race. Upper frame portion 102 supports the opposite end of optical assembly 103 by outer race 104 in combination with ball bearings 105 and upper lens mount 106 with machine surface 107 acting as an inner race. Upper lens mount 106 is joined to lower lens mount 110 by cylinder 112 which maintains constant spacing between the lens mounts and provides concurrent rotation thereof. Carriage 113 is slideably mounted in cylinder 112. Follower 115 engages ring 114 which is connected to carriage 113 through slots 120. As optical assembly 103 is rotated, groove 19 in ring 114 engages pin 116 to slide carriage 113 in cylinder 112 as follower 115 is moved by threaded shaft 117. Threaded shaft 117 is turned rotatably in either direction by cylinder motor 118.

What is claimed is:

1. In an apparatus having a member moveable in first and second directions along a first path, a reference position along said first path, drive means to move said member along said first path in either of said first and second directions and selectively activatable control means operably connected to said drive means for returning said member to said reference position, the improvement comprising, an occluder connected to said member and moveable along a second path in response to movement of said member, one end of said occluder being positioned at a location along said second path when said member is at said reference position, an energy beam interesecting said second path at said location, detecting means for detecting said energy beam and including signal generating means, said occluder interrupting said energy beam when said member is spaced from said reference position in said first direction, said control means, when activated, stopping said drive means in response to a change in the signal from said generating means and said control means, when activated, driving said member in said first direction when said signal indicates the presence of said energy beam and driving said member in said second direction when said signal indicates the absence of said energy beam.

2. the improvement of claim 1 wherein said first and second paths are straight.

3. The improvement of claim 2 wherein said first and second paths are parallel.

4. The improvement of claim 1 wherein said refernce position is substantially intermediate said first path, and said location is substantially intermediate said second path.

* * * * *